United States Patent [19]

Knight et al.

[11] Patent Number: 5,380,646
[45] Date of Patent: Jan. 10, 1995

[54] THROMBUS DETECTION USING RADIOLABELLED DISINTEGRINS

[75] Inventors: Linda C. Knight, Moorestown, N.J.; Alan H. Maurer, Wynnewood, Pa.

[73] Assignee: Temple University of the Commonwealth System of Higher Education, Philadelphia, Pa.

[21] Appl. No.: 965,674

[22] Filed: Oct. 19, 1992

[51] Int. Cl.6 .................. A61K 49/02; G01N 33/53
[52] U.S. Cl. ...................... 424/1.69; 514/12; 424/9
[58] Field of Search .............. 519/12; 424/1.1, 9; 435/7.21; 530/326, 325, 324

[56] References Cited

U.S. PATENT DOCUMENTS 5,066,592 11/1991 Huang et al. ............... 430/240.2

FOREIGN PATENT DOCUMENTS 0333356 9/1989 European Pat. Off. .
0338634 10/1989 European Pat. Off. .
0382451 8/1990 European Pat. Off. .
WO90/15818 12/1990 WIPO .

OTHER PUBLICATIONS

Gould et al., *Proc. Soc. Exp. Bio. Med.* 195:168 (1990).
Knight et al., *J. Nucl. Med.* 31:757 (abstr.) (1990).
Knight, L. C., *Sem. Nucl. Med.* 20:52 (1990).

*Primary Examiner*—Esther M. Kepplinger
*Assistant Examiner*—Lora M. Green
*Attorney, Agent, or Firm*—Seidel, Gonda, Lavorgna & Monaco

[57] ABSTRACT

Radiolabelled polypeptides derived from the Viperidae disintegrins are provided as well as a method for the detection of venous and arterial thrombi, pulmonary emboli and tumors or abscesses that have a thrombus component. Compositions suitable for parenteral administration comprising the radiolabelled polypeptides and a pharmaceutically acceptable carrier are also provided.

27 Claims, 1 Drawing Sheet

THROMBUS DETECTION USING RADIOLABELLED DISINTEGRINS

FIELD OF THE INVENTION

The invention relates to the imaging of vascular thrombi and emboli.

BACKGROUND OF THE INVENTION

Thromboembolic disease is a common human physiological disorder, with about 2.5 million cases per year arising in the United States alone. Thrombi are manifested by the partial or total occlusion of blood vessels by the formation of deposits of platelets, fibrin and other blood elements. Emboli are portions of thrombi that have broken away from the site of their formation and lodged in small blood vessels, such as the vessels of the lungs or the brain. Acute vascular diseases, including pulmonary embolism, deep venous thrombosis (DVT), peripheral arterial occlusion, myocardial infarction and other blood system thrombi constitute major health risks. Safe and accurate detection of the presence and location of intravenous thrombi in the human body is required for disease diagnosis, prognosis and effective treatment. Some forms of thrombosis, such as DVT, are virtually undetectable at early stages due to highly unreliable clinical signs. Because of the potential risk or morbidity and mortality, early detection and treatment of thromboembolic diseases are of paramount importance. Anticoagulant therapy is available for treatment of thromboembolic disorders, but poses additional risks such as hemorrhaging and thrombocytopenia. Therefore anticoagulants should not be used without a justifiable level of medical certainty confirming the presence of thrombi.

Detection of Thrombi

An ideal radiopharmaceutical for detecting vascular thrombi should be able to specifically and rapidly locate thrombi without interference by anticoagulants. Methods of thrombus detection under investigation include labelling of platelets, as well as the labelling of chemically modified plasma proteins and monoclonal antibodies specific for thrombi. The current commonly used nuclear medicine imaging tests for DVT are based on the use of nonspecific radiopharmaceuticals to perform radionuclide venography. These nonspecific radiopharmaceuticals include a $^{99m}$Tc sulfur colloid, as well as macroaggregated albumin and autologous erythrocytes also labelled with $^{99m}$Tc. These agents merely provide blood pool images that may indicate filling defects at the site of occlusion. They do not indicate focal uptake by thrombi. Radionuclide venography is the only nuclear medicine imaging method currently in use for detecting venous thrombi. It uses easily prepared and approved radiopharmaceuticals that are available to non-research institutions.

Venous thrombi are composed primarily of polymers of fibrin with entrapped blood cells, alternating with layers of aggregated platelets held together with fibrin. Arterial thrombi are composed mainly of aggregated platelets, with a lesser amount of fibrin. In the search for radiolabelled compounds to use as probes for thrombi in vivo, investigators have studied molecule that bind to fibrin. One of the compounds studied most extensively has been fibrinogen, which becomes converted to fibrin in vivo and is incorporated into the matrix of a thrombus as it forms. $^{125}$I labelled fibrinogen has provided the basis of a nonimaging screening test, the Fibrinogen Uptake Test (FUT), which is used for newly forming thrombi. $^{125}$I Human fibrinogen is injected intravenously into patients at risk for developing DVT. Subsequently, a hand-held scintillation detector is used to monitor counts at marked points along the patient's body. However, the low-energy gamma rays associated with $^{125}$I do not permit thrombus imaging. The counting data is also unreliable, especially in critical body areas due to scattered radiation from organs and signal attenuation from overlying tissue. It is generally believed that some of the thrombi not accurately detected by this test pose the greatest risk for significant pulmonary embolism. Wheeler et al., *Chest* 89:497S–412S (suppl.) (1986). The Fibrinogen Uptake Test is insensitive for preformed thrombi (Coleman et al., *J. Nucl. Med.* 16:370–373 (1975)) and is incompatible with the simultaneous use of anticoagulants since they interfere with the incorporation of labelled fibrinogen into nascent thrombi (Mant et al., *Arch. Intern. Med.* 141:1757–1760 (1981)).

Several investigators have attempted to develop procedures for radiolabelling fibrinogen with $^{99m}$Tc. A labelling procedure reported by Jeghers et al. seems to provide a stable label and long life in vivo. Jeghers et al., *Eur. J. Nucl. Med.* 3:95–100 (1978). However, Jonckheer et al., *Eur. J. Nucl. Med.* 3:233–238 (1978) caution that the in vivo signal can be nonspecific and is a potential cause of false results. Therefore, drawbacks of this method are much the same as those for blood pool nonspecific radiotracers. $^{99m}$Tc has a short physical half-life while fibrinogen has a long lifetime in vivo. By the time the blood background has cleared sufficiently for the target-to-background ratio to be high enough to permit visualization of the thrombus, the count rate may be too low from physical decay for effective imaging. Moreover, because of its long residence in the blood, fibrinogen is not a suitable conjugate for an acceptable quick diagnostic procedure, that is, a procedure with an imaging time of under 4 hours.

Polyclonal antibodies reactive with fibrinogen as well as fibrin have been investigated as tools to detect thrombi in vivo. Spar et al., *Circ. Res.* 17:322–329 (1965). Partially due to the antibodies' long residence time in the blood, these methods were found to be ineffective and resulted in a long delay (24 to 48 hours) before images could be obtained. Monoclonal antibodies are now being studied for imaging deposits of fibrin. Hui et al., *Science* 222:1129–1132 (1983; Rohoza et al., *Mol. Immunol.* 21:89–94 (1984). It has been demonstrated that Fab' fragments of an antifibrin monoclonal antibody labelled with $^{99m}$Tc were capable of producing images of fresh thrombi in dogs within 1 to 2 hours post-injection. Knight et al., *Radiology* 173:163–169 (1989); Knight et al., *J. Nucl. Med.* 29:746 (abstr.) (1988). But, anticoagulants such as heparin present a problem similar to that in the Fibrinogen Uptake Test. They tend to decrease monoclonal antibody binding to fibrin. A final serious disadvantage of medically applied murine monoclonal antibodies is the potential risk to a patient's anaphylaxis hypersensitivity response to such injections.

Other biomolecules involved in blood clotting or dissolution have been used only with marginal success in their ability to image thrombi. Included are the plasminogen activators urokinase, streptokinase and tissue plasminogen activator. Krohn et al., *Semin. Nucl. Med.*

7:219-228 (1977). Heparin, equally has not been found successful as an agent for imaging thrombi. Utne et al., *Eur. J. Nucl. Med.* 6:237-240 (1981). Fibronectin has not been useful for imaging pulmonary emboli probably because of competition from endogenous, nonlabelled fibronectin in the blood. Zoghbi et al., *Invest. Radiol.* 23:574-578 (1988).

Platelet labelling has also been used in attempts to image platelet deposits. Thakur et al., *Thromb. Res.* 9:345-357 (1976). Imaging of thrombi with radiolabelled platelets usually requires a delay of 24 to 72 hours, due to the prolonged circulation time of platelets and resulting high blood background. Platelets accumulate in the liver and spleen. Concentrations of radiolabel in the liver and spleen provide a high background, near which it is difficult to image pulmonary emboli. In addition, anticoagulants tend to interfere with the incorporation of labelled platelets into thrombi which thereby yield false negatives upon attempted imaging.

Monoclonal antibodies that bind human platelets have also been tested for their ability to image thrombi. Coller et al., *J. Clin. Invest.* 72:325-338 (1983); Stuttle et al., *Nucl. Med. Commun.* 9:647-655 (1988); Palabrica et al., *Proc. Natl. Acad. Sci. USA* 86:1036-1040 (1989). This technique is an advance over the laborious cell isolation and washing procedure required for the labelling of platelets. A disadvantage of monoclonal antibodies is that they are exceptionally large molecules. Typically around 180 kd or more, their size contributes to their immunogenicity in humans, and potential for allergic reaction. If the antibodies bind to circulating, i.e., resting, platelets, this prolongs residence in the blood pool and delays the time to imaging for 24 hours or more.

Synthetic Peptides

International Patent Application WO 90/15818 is directed to radioactively labelled synthetic peptides of 3-10 amino acids containing an Arg-Gly-Asp sequence for detection of tumors and thrombi in mammals.

European Patent Application 333,356 is directed to synthetic peptide analogs of between about 8-26 amino acids derived from the naturally occurring leech anticoagulant hirudin and their use in the treatment, prevention or in vitro diagnosis of vascular disease. The hirudin peptides recommended for radiolabelling for thrombus imaging do not include the Arg-Gly-Asp sequence.

Small Arg-Gly-Asp-containing peptides such as those described in WO 90/15818 and Knight et al., *J. Nucl. Med.* 31:757 (1990) (abs.) lack sufficient biospecificity to result in effective imaging of thrombi. In particular, no radiotracer to date has been successfully used in imaging pulmonary emboli. In some cases, the radiolabel accumulates in the liver or remains circulating in the cardiac blood pool, and thereby obscures images of the lung. More importantly, there is inadequate deposition of tracer in the emboli. Hence pulmonary emboli have not been imaged using small Arg-Gly-Asp-containing peptides.

There are essentially four characteristics of a radiotracer which impact on its ability to provide rapid images of emboli or thrombi:

(1) Affinity—The radiotracer should bind avidly, nonreversibly and in high concentration to the surface of a thrombus or embolus.

(2) Specificity—The radiotracer must not bind to normal tissues, such as normal vascular endothelium.

(3) Route of excretion—Radiotracers are usually excreted by either the liver or the kidneys. Radioactivity removed from the blood will concentrate for a time in the liver or the kidneys before being eliminated from the body in feces or urine, respectively. For imaging pulmonary emboli, it is preferably for the route of excretion to be via the kidneys, because they are far from the lungs. Concentration of radioactivity in the liver will provide high background near which it is difficult to image pulmonary emboli.

(4) Blood clearance rate—The rate should be rapid enough so that the blood background will be low when the images are taken. In the case of imaging thrombi in the extremities, this is useful to minimize false readings. A rapid clearance rate is even more important in the case of pulmonary emboli, because the cardiac blood pool is adjacent to the lungs, and a large bright area can obscure areas of faint uptake.

None of the imaging agents proposed thus far satisfy all of these requirements. While the small RGD-containing peptides appear to be satisfactory from the standpoint of excretion route and blood clearance rate, they lack high affinity for thrombi and emboli, and lack specificity for those targets. What is needed is an imaging agent fulfilling all of the above-listed criteria.

The Disintegrins

Integrins are cell membrane glycoproteins which function as cell surface receptors in the orchestration of biophysical recognition and cellular biochemical interactions. Integrins, including the platelet fibrinogen receptor GP IIb/IIIa, are present in membranes of platelets, endothelial cells and fibroblasts which are directly involved in the physiology of thrombi formation. Many biochemical messenger and structurally interactive molecules involved in thrombus formation such as fibronectin, vitronectin, osteopontin, collagens, thrombospondin, laminin, fibrinogen and the von Willebrand factor contain the tripeptide sequence Arg-Gly-Asp which has been characterized as a recognition site for the common integrins. Ruoslahti et al., *Science* 238:491-497 (1987).

Disintegrins are low molecular weight proteins from the Viperidae family of snakes which bind the integrins discussed above similar to the endogenous messenger and structurally interactive biomolecules. Disintegrins thus in vitro are competitive inhibitors of the biomolecules such as fibrinogen for integrin binding sites such as Gp IIb/IIIa on human platelets. Disintegrins, similar to the endogenous functional integrin-binding biomolecules contain the tripeptide sequence Arg-Gly-Asp.

Amino acid sequences of several disintegrin viper venom peptides have been reported, as summarized by Gould et al., *Proc. Soc. Exp. Bio. Med.* 195:168 (1990). U.S. Pat. No. 5,066,592 is directed to the disintegrin trigramin, its preparation and its utility as an inhibitor of fibrinogen induced human platelet aggregation. Other disintegrins are disclosed in European Patent Application Nos. 338,634 and 382,451. Although described for therapeutic use, disintegrins have not heretofore been recognized as having utility in diagnostic imaging.

SUMMARY OF THE INVENTION

A composition suitable for parenteral administration comprises a pharmaceutically acceptable carrier and at least one radiolabelled polypeptide having the amino acid sequence:

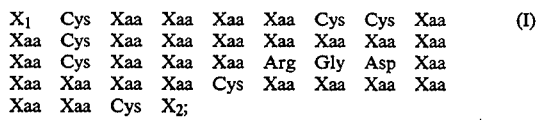

wherein each Xaa, either the same or different, is any amino acid; $X_1$ is at least one amino acid, either the same or different; and $X_2$ is at least one amino acid, either the same or different.

In a preferred embodiment, the radiolabelled polypeptides according to formula (I) have the amino acid sequence:

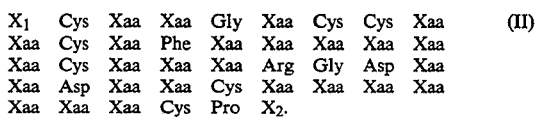

wherein Xaa, $X_1$ and $X_2$ are defined as in formula (I).

In another preferred embodiment, the radiolabelled polypeptides according to formula (II) have the amino acid sequence:

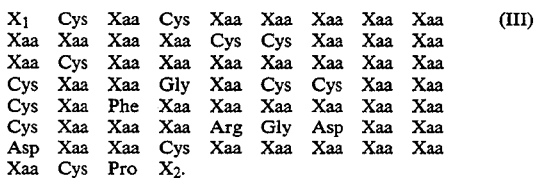

wherein Xaa, $X_1$ and $X_2$ are defined as in formula (I).

In another embodiment the radiolabelled polypeptides according to formula (III) have been the sequence:

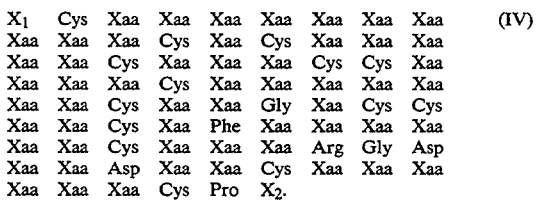

wherein Xaa, $X_1$ and $X_2$ are defined as in formula (I).

In yet another embodiment the radiolabelled polypeptides according to formula (I) have the sequence:

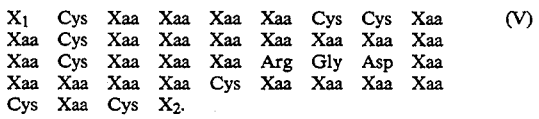

wherein Xaa, $X_1$ and $X_2$ are defined as in formula (I).

In another preferred embodiment the radiolabelled polypeptides according to formula (II) have the sequence:

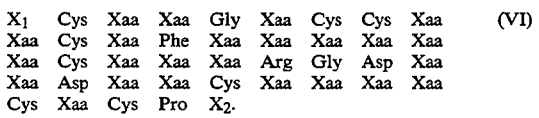

wherein Xaa, $X_1$ and $X_2$ are defined as in formula (I).

The radiolabelled polypeptides include, but are not limited to, disintegrins derived from the Viperidae family of snakes: bitistatin 1, bitistatin 2, bitistatin 3 and bitistatin 4 from *Bitis arietans* (SEQ ID NOS:1-4); trigramin from *Trimeresurus gramineus* (SEQ ID NO:5); echistatin from *Echis carinatus* (SEQ ID NO:6); eristostatin from *Eristocophis macmahoni* (SEQ ID NO:7); batroxostatin from *Bothrops atrox* (SEQ ID NO:8); agkistrostatin (SEQ ID NO:9) and applagin (SEQ ID NO:10) from *Agkistrodon piscivorous*; rhodostomin from *Agkistrodon rhodostoma* (SEQ ID NO:11); elegantin from *Trimeresurus elegans* (SEQ ID NO:12); flavoridin from *Trimeresurus flavoviridis* (SEQ ID NO:13) and albolabrin from *Trimeresurus albolabris* (SEQ ID NO:14).

The invention is also directed to a method for detecting venous and arterial thrombi, pulmonary emboli and tumors or abscesses that have a thrombus component, comprising: administering to a patient at least one radiolabelled polypeptide according to the invention; and scintigraphically imaging the radiolabelled polypeptides.

DETAILED DESCRIPTION OF THE INVENTION

Figure 1:
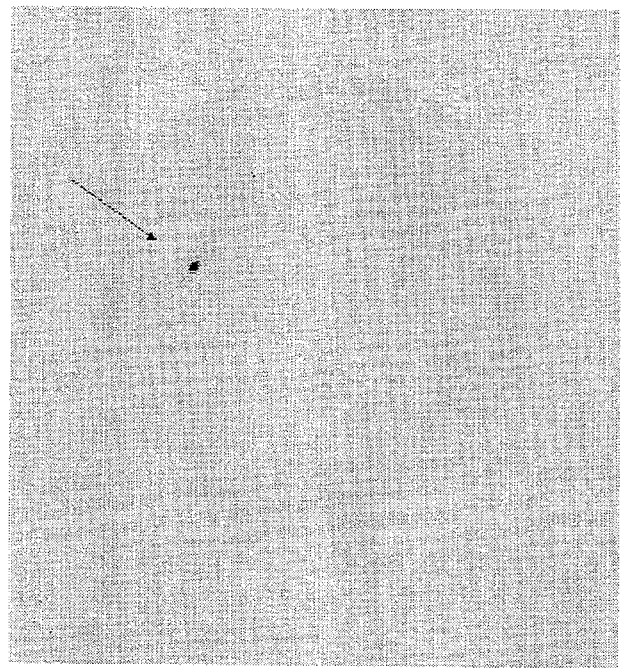
FIG. 1 is an image of both hind legs of a dog 2 hours after injection of the radiolabelled disintegrin $^{123}$I-bitistatin. There is clear focal uptake of radiotracer in the induced thrombus.

The invention comprises the parenteral administration of at least one radiolabelled polypeptide disclosed herein and the subsequent detection of the presence and location of the label with imaging technology well known to those of ordinary skill in the art of nuclear medicine. Freeman et al., *Freeman and Johnson's Clinical Radionuclide Imaging* 3, (1) (1984) Grune & Stratton, New York; Ennis et al., *Vascular Radionuclide Imaging: A Clinical Atlas*, John Wiley & Sons, New York (1983).

This invention is directed to a series of novel radiopharmaceuticals having utility in low dosage and significantly increased specificity for thrombus detection. The invention enables improved accuracy and decreased background signal in ex vivo imaging of deep venous thrombi and in the previously unsuccessful imaging of pulmonary emboli. The invention also enables imaging of tumors and abscesses which contain thrombus components such as fibrin and activated platelets.

The labelled disintegrins disclosed herein represent a significant advance in nuclear medicine for the need to carry detectable label rapidly and specifically to thrombi without interference by anticoagulants. Because of the disintegrins' specificity for thrombi and their rapid rate of clearance from the blood, a rapid and objective method for disease diagnosis is available with increased accuracy.

The radiolabelled disintegrins are superior to radiolabelled fibrinogen and other available radiopharmaceuticals in binding to thrombi. Of particular significance is the fact that the labelled disintegrins have low affinity for binding normal vascular endothelia. Nonspecific binding to normal endothelia is a disadvantage of small synthetic Arg-Gly-Asp-containing peptides which have been suggested as thrombus targeting vehicles, such as those described in WO 90/15818 and Knight et al., *J. Nucl. Med.* 31:757 (1990) (abs.). The radiolabelled disintegrins are further characterized by low uptake by the lung and liver tissue. This advantage has permitted for the first time effective imaging of pulmonary emboli.

Deep venous thrombi are clearly visible following the administration of radiolabelled disintegrins. Using $^{123}$I-bitistatin, for example, imaging is possible as soon as twelve minutes post-injection. In contrast to most radiotracers, the radiolabelled disintegrins are demonstrated to be capable of binding to both actively forming and pre-formed thrombi. The important characteristic of low background uptake in the injured vessel, control vessel and normal lung is also demonstrated with radiolabelled disintegrins. Residual levels in the blood and muscle are low, resulting in high clot:blood and clot:muscle target:background ratios. All tested radiolabelled disintegrins clearly demonstrate higher binding to thrombi than short Arg-Gly-Asp-containing peptides. Of particular significance, target-to-background ratios for the radiolabelled disintegrins are within the medically acceptable range for diagnostic imaging. The short Arg-Gly-Asp-containing peptides which have been tested are not within the acceptable range. The unexpected superior imaging of DVT and pulmonary emboli is believed due to the GP IIb/IIIa apparent biological preference for the molecular "skeleton" of the disintegrins.

The invention differs from the small Arg-Gly-Asp-containing peptides described in International Patent Application WO 90/15818 in that the disintegrins contain a biologically evolved cysteine skeleton which, without wishing to be bound by any theory, provides significantly more stable binding to thrombi than the smaller peptides which lack the cysteine skeleton. The radiolabelled disintegrins specifically bind thrombi with high affinity.

The disintegrins as a group are characterized by seven unanimously conserved cysteine residues. These seven residues, with the glycine residue of the Arg-Gly-Asp sequence being designated as zero, conform to positions: $-23$, $-18$, $-17$, $-14$, $-5$, $+7$ and $+14$. The disintegrins are further characterized by four unanimously conserved amino acids at the following positions: glycine at $-20$; phenylalanine at $-12$; aspartic acid at $+4$; and proline at $+51$.

Additional conserved cysteine residues appear in the larger disintegrins at positions $-31$, $-36$, $-37$, $-47$, $-49$ and $-60$ as the length of the disintegrin polypeptides progressively increase.

While some of the disintegrins may contain a cysteine residue at position $-41$, e.g., bitistatins 1-4 (SEQ ID NOS:1-4, respectively), such is not required for the practice of the invention. Disintegrins which do not contain cysteine at position $-41$ include, for example: trigramin (SEQ ID NO:5), batroxostatin (SEQ ID NO:8), agkistrostatin (SEQ ID NO:9), applagin (SEQ ID NO:10), rhodostomin (SEQ ID NO:11), elegantin (SEQ ID NO:12), flavoridin (SEQ ID NO:13) and albolabrin (SEQ ID NO:14).

Disintegrins under 50 amino acids in length, useful in the practice of the invention, include but are not limited to echistatin (SEQ ID NO:6) and eristostatin (SEQ ID NO:7), each of which contains a cysteine residue at position $+12$.

Disintegrins which contain cysteine amino acid residues at least at positions $-23$, $-18$, $-17$, $-14$, $-5$, $+7$ and $+14$ are represented by the formula:

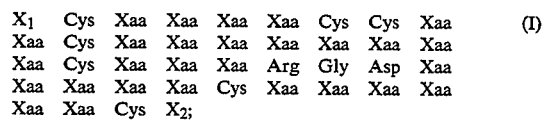

wherein each Xaa, either the same or different, is any amino acid; $X_1$ is at least one amino acid, either the same or different; and $X_2$ is at least one amino acid, either the same or different.

Other useful disintegrins preferably further contain the following conserved amino acids: glycine at position $-20$; phenylalanine at position $-12$; aspartic acid at position $+4$; and proline at position $+15$. These preferred polypeptides are defined according to the formula:

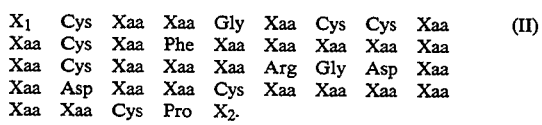

wherein Xaa, $X_1$ and $X_2$ are defined as in formula (I).

Another group of disintegrins useful in the practice of the invention comprises the polypeptides according to formula (II) which are further characterized by cysteine residues at positions $-31$, $-36$, $-37$, $-47$, and $-49$ as their progressive length in the direction of the amino terminus increases. These polypeptides are defined according to the formula:

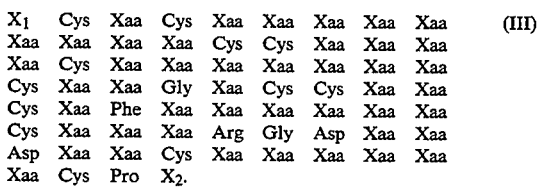

wherein Xaa, $X_1$ and $X_2$ are defined as in formula (I).

Yet another group of preferred disintegrins includes the polypeptides according to formula (III) which are further characterized by a cysteine residue at position $-41$ and another cysteine at position $-60$ as the progressive length in the amino terminal direction permits. These larger polypeptides are defined according to the formula:

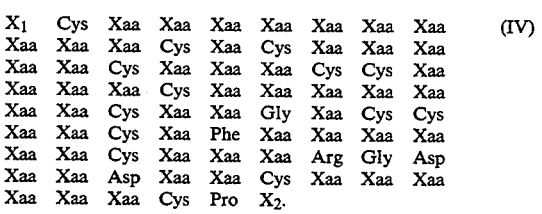

wherein Xaa, $X_1$ and $X_2$ are defined as in formula (I).

Preferred radiolabelled polypeptides comprising less than 50 amino acids in length include those polypeptides according to formula (I) which contain cysteine at position +12. These polypeptides are defined according to the formula:

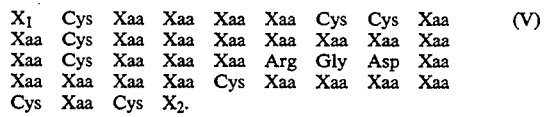

wherein Xaa, $X_1$ and $X_2$ are defined as in formula (I).

Other preferred polypeptides comprising less than 50 amino acids include the polypeptides according to formula (II) which contain cysteine at position +12. These polypeptides are defined according to the formula:

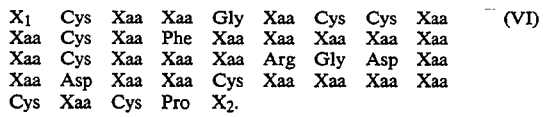

wherein Xaa, $X_1$ and $X_2$ are defined as in formula (I).

For thrombus detection, polypeptides from about 40 to about 450 amino acids in length, corresponding to a molecular weight of about 4,200–50,000 daltons before the addition of a detectable label, are particularly preferred. Polypeptides larger than about 50,000 daltons might remain in the blood pool too long. Preferably, the polypeptide is from about 40 to about 90 amino acids in length, corresponding to a molecular weight of about 4,200–10,000 daltons before the addition of the label. The polypeptide may comprise a single chain of amino acids, or may comprise multiple chains of identical or nonidentical sequences of amino acids. The polypeptide may comprise a radiolabelled dimer, trimer or multimer of the same or different disintegrin molecule, at least one of which carries an appropriate radiolabel for imaging. Thus, as used herein, the expression "polypeptide" when referring to the imaging vehicle of the present invention, includes not only molecules comprising single chains of amino acids but also molecules comprising aggregates of more than one chain, which chains may be linked together by covalent or noncovalent bonds.

Preparation of Labelled Disintegrins

The disintegrins may be isolated in a substantially pure form from their respective Viperidae sources. Generally the Viperidae disintegrins are purified from lyophilized venoms (i.e. from Miami Serpentarium Laboratories, Salt Lake City, Utah) by a three step procedure of gel filtration, ion exchange chromatography, and reverse phase C18 high performance liquid chromatography (HPLC). Huang, et al., *J. Biol. Chem.* 262:16157–16163 (1987); Huang, et al., *Biochemistry* 28:661–666 (1989); Gan, et al., *J. Biol. Chem.* 262:19827–19832 (1988); Shebusky, et al., *J. Biol. Chem.* 264:21550–21556 (1989). Alternatively, purification from crude venom can be achieved by two cycles of reverse phase HPLC.

The disintegrins may be isolated from lyophilized venom as follows. Lyophilized venom may be dissolved in 10 mM ammonium bicarbonate, pH 7.7 containing 20 mM DTT, followed by elution on a Sephadex G-50 column with 10 mM MES, pH 5.3. After desalting on a Sephadex G-15 column the protein may be loaded on a Mono S FPLC column and fractionated with a linear NaCl gradient. Pooled activity fractions may then be loaded on a C18 reverse phase HPLC column for further purification. Homogeneity of the eluted proteins may be characterized by SDS polyacrylamide gel electrophoresis and rechromatography on reverse phase HPLC.

The disintegrins may also be purified to chemical homogeneity from lyophilized venom of respective Viperidae by means of reverse phase HPLC according to Williams, et al., *Biochim. Biophys. Acta* 1039:81–89 (1990) and European Patent Application 382,451. The disintegrin trigramin may be purified to chemical homogeneity for labelling from the venom of *Trimeresurus gramineus* by means of reverse phase HPLC according to U.S. Pat. No. 5,066,592. The entire disclosures of U.S. Pat. No. 5,066,592 and European Patent Applications 338,634 and 382,451 are incorporated herein by reference.

Those of ordinary skill in the art may also produce the disintegrins by well known biosynthetic means via corresponding gene expression in heterologous host systems. Gan et al., *Gene* 79:159–166 (1989); Jacobson et al., *Gene* 85:511–516 (1989). The amino acid sequences of the individual disintegrins may readily be used to construct synthetic genes which encode the specific disintegrins and variations thereof as herein described for biological expression. Even though at times eucaryotic genes expressed in bacteria yield unstable polypeptides, frequently the genes are fused to native bacterial genes in order to create stable chimeric biosynthetic proteins. The chimeric proteins are easily isolated by immunoaffinity chromatography and the active polypeptide is released by subsequent site-specific proteolytic cleavage. Well developed commercial bacterial expression vectors and host cells are readily available as well as isolation/purification materials and protocols for production of these biosynthetic polypeptides (i.e. Protein Fusion and Purification System (PFP), New England Biolabs). European Patent Applications 338,634 also presents a clear overview of disintegrin biosynthesis in bacterial systems.

The disintegrins may also be synthesized in vitro by chemical coupling and end-product purification methods well known to those of ordinary skill in the art. See, Garsky, et al., *Proc. Natl. Acad. Sci. USA* 86:4022–4026 (1989). Polypeptides of the invention may be prepared using solid phase synthesis, such as that described by Merrifield, *J. Am. Chem. Soc.* 85:2149 (1964). Other equivalent chemical syntheses known in the art can also be used, such as the synthesis of Houghten, *Proc. Natl. Acad. Sci.* 82:5132 (1985). Solid-phase synthesis is commenced from the C-terminus of the peptide by coupling a protected amino acid to a suitable resin, as generally set forth in U.S. Pat. No. 4,244,946, the disclosure of which is incorporated herein by reference. Examples of syntheses of this general type are set forth in U.S. Pat. Nos. 4,305,872 and 4,316,891. Solid-phase synthesis of large polypeptides is also described by Vale et al., *Science* 213:1394–1397 (1981). A more detailed discussion of the synthesis of larger peptides appears in an article by Marke et al., in *J. Am. Chem. Soc.* 103:3178 (1981).

Throughout this specification and in the claims, the abbreviations employed for amino acids and their residues are used in conformity with the generally accepted rules of nomenclature and relate to α-amino acids and their residues of the L-series. However, the present invention also relates to the D-retro forms of the peptides described herein. These are produced by synthesis with D amino acids in the opposite orientation, beginning with the carboxy terminal amino acid of the L form.

Derivatization of the peptides of the invention may involve the addition of a negatively charged side group onto either the free phenolic hydroxyl or the benzoyl meta carbon of the single tyrosine residue. The derivatization may involve the addition of a variety of negatively charged side groups which are known in the art. Derivatization methods include, but are not limited to, sulfation, methyl sulfonation, phosphorylation, methyl phosphonation and carboxylation of the tyrosine hydroxyl group and sulfonation, phosphonation and carbonation of the tyrosine benzoyl meta carbon. Techniques for performing these reactions are also well known in the art.

A wide range of radioactive species may be employed for providing the radioactive label for use in the invention. Suitable radioactive labels include, but are not limited to $^{99m}Tc$, $^{123}I$, $^{111}In$, $^{68}Ga$, $^{18}F$, $^{125}I$, $^{131}I$, $^{113m}In$, $^{76}Br$ and $^{67}Ga$. $^{99m}Tc$, $^{123}I$, $^{111}In$, $^{68}Ga$, and $^{18}F$ are preferred. Radioactive atoms can be attached to peptides and proteins by methods well known to those skilled in the art. See, Science 220:613–615; Int. J. Nucl. Med. Biol. 12:3–8; J. Nucl. Med. 27:685–693 and J. Nucl. Med. 26:293–299. Arano et al., Bioconjugate Chemistry 2:71–76 (1991); Eisenhut et al., J. Labelled Comp. Radiopharm 30:198–199 (1991) (abs.); Garg et al., Bioconjugate Chemistry 2:44–49 (1991); Knight et al., Thromb. Haemostas 46:593–596 (1981); Mather et al., J. Nucl. Med. 31:692–697 (1990).

The peptides disclosed herein may also be modified for attachment of metallic radiolabels by addition of bifunctional chelating groups. Krejcarek et al., Biochem Biophys Res. Commun. 77:581–585 (1977); Fritzberg et al., Proc. Natl. Acad. Sci. USA 85:4025–4029 (1988); Sundberg et al., Nature 250:587–588 (1974); Bhargava et al., J. Labelled Comp. Radiopharm. 30:216–218 (1991) (abs.); Benisek et al., J. Biol. Chem. 243:4267–4271 (1968).

The radiolabelled disintegrins may be combined with any pharmaceutically acceptable carrier suitable for parenteral, preferably intravenous administration. Thus, the radiolabelled polypeptides may be formulated according to conventional methods for preparing polypeptide agents for parenteral administration. The intravenous carrier most advantageously comprises a pharmaceutically acceptable buffer solution such as phosphate buffered saline, preferably in combination with a pharmaceutically acceptable compound for adjusting isotonic pressure, such as mannitol or sorbitol.

Compositions for parenteral administration, including intravenous injection, may be in the form of lyophilizates or solutions. The resulting formulations will contain an amount of the radiolabelled polypeptides effective for imaging thrombi.

The concentration of radiolabelled polypeptides in the composition is not critical to practice the method of invention. When administered as a bolus injection to an average 70 kg human, the concentrations of labelled polypeptides preferably range from about 0.1 to about 3 mg/ml (weight of labelled polypeptide per volume of composition). When administered as a slow infusion into the bloodstream, effective concentrations of the labelled polypeptides include but are not limited to about 1 to about 30 μg/ml.

The effect of radiolabelling the disintegrins depends upon the particular radionuclide used. The radiation dosimetry, which depends upon the biodistribution kinetics of the particular radionuclide used, is easily determined by those skilled in the art of nuclear medicine. Methods for determining the appropriate degree of radiolabelling are known to those skilled in the art.

Practical dosages of disintegrins labelled with preferred radionuclides for single administration to a 70 kg standard sized human are expressed in terms of the mass of labelled polypeptide and amount of radioactivity. Practical dosages of disintegrins radiolabelled with preferred radionuclides are as follows:

| Radionuclide | Range of Radioactivity | Mass of Labelled Polypeptide |
|---|---|---|
| $^{99m}Tc$ | 2–50 mCi (10–30 mCi preferred) | 50 μg–2 mg (300 μg–700 μg preferred) |
| $^{123}I$ | 1–30 mCi (5–20 mCi preferred) | 5 μg–1 mg (30 μg–70 μg preferred) |
| $^{111}In$ | 0.1–7 mCi (1–3 mCi preferred) | 5 μg–1 mg (50 μg–150 μg preferred) |
| $^{68}Ga$ | 0.1–7 mCi (1–3 mCi preferred) | 5 μg–1 mg (50 μg–150 μg preferred) |
| $^{18}F$ | 1–20 mCi (5–15 mCi preferred) | 5 μg–1 mg (300 μg–700 μg preferred) |

The rate of administration of radiolabelled disintegrin and the total dosage depends on a variety of factors such as the particular disintegrin employed to carry the radiolabel. The dosage may range, for example, from about 1 μg to about 2 mg of radiolabelled polypeptide per patient dose. Most preferably, the dosages range from about 5 μg to about 1 mg per patient dose. As used herein, the term "patient" includes both humans and animals.

The composition may additionally contain components which are effective in fibrinolytic therapy. These include, but are not limited to, tissue plasminogen activator, urokinase and streptokinase. These other compounds may be present as separate components in the composition, or it may be attached covalently to the disintegrin.

Method of Use

The radiolabelled polypeptides are preferably intravenously injected for subsequent ex vivo imaging of venous thrombi, arterial thrombi, pulmonary emboli and tumors and abscesses that have a thrombus component.

Methods for imaging radionuclides in vivo are well known to those skilled in the art. Details regarding methods of imaging radionuclides in vivo and vascular imaging in particular are available in standard textbooks. Freeman et al., Freeman and Johnson's Clinical Radionuclide Imaging, 3rd. ed. Vol. 1 (1984) Grune & Stratton, New York; Ennis et al. Vascular Radionuclide Imaging: A Clinical Atlas, John Wiley & Sons, New York (1983).

According to a method of ex vivo imaging of deep venous thrombi, at least one radiolabelled disintegrin is injected or infused into a peripheral vein such as the antecubital of the patient. A gamma camera is used to externally follow the distribution of the imaging agent in the patient's body. Anterior and posterior images of the legs are acquired immediately after injection, and repeat images are taken at one or more intervals during the first 6 hours after injection. An image indicative of the presence of thrombi or emboli exhibits "hot spots" (foci of radiotracer accumulation).

For imaging of pulmonary emboli, images of the chest are obtained in a number of different projections, including anterior, posterior, lateral and oblique views.

The images are acquired at one or more intervals between 1 and 6 hours post injection. Emboli are apparent as focal areas of radiotracer uptake in the pulmonary arteries. Due to the specificity of the disintegrins for the emboli, the radiolabelled disintegrins do not substantially accumulate in the liver, heart or lung tissue, which would otherwise obscure images of pulmonary emboli. Pulmonary emboli are clearly imaged and are not obscured by such surrounding background.

Techniques for imaging thrombi and emboli may be varied for the purpose of imaging tumors and abscesses. In particular, other areas of the body where tumors or abscesses are suspected to reside can be imaged. Anterior and posterior views can be used as well as abdominal or surveys of the entire body. Alternatively, tomographic images may be acquired using a SPECT (Single Photon Emission Computed Tomography) or PET (Positron Emission Tomography) camera. These techniques are described in *Freeman and Johnson's Clinical Radionuclide Imaging* textbook referenced above.

The practice of the invention is illustrated by the following non-limiting examples.

EXAMPLE 1

Preparation of $^{123}$I Bitistatin

A 100 µg solution of the native bitistatins, in 100 µl 0.05M Tris buffer pH 7.8, containing 0.1M NaCl, was drawn up by syringe and added to a vial containing 9.75 mCi $^{123}$I sodium iodide solution in a volume of 27 µl (Nordion Co., Canada). This mixture was transferred to a microfuge tube coated on the inside walls with 100 µg Iodogen (1,3,4,6-tetrachloro-3α,4α-diphenylglycoluril) and capped with a red rubber serum stopper. The reaction was allowed to stand at room temperature for 30 minutes. After this time, the radiochemical purity of the radiolabeled peptide was assessed by spotting a 2 µl sample of the reaction mixture on a strip of Instant Thin Layer Chromatography media (ITLCSG). The spot was allowed to air-dry, and then the strip was developed in 85% methanol. The strip was cut in half, the two segments were counted in a NaI(Tl) well counter (Searle, Des Plaines, Ill.). The net counts on each half of the strip were computed by subtracting the background counts from the gross counts. The percentage of added radioiodine which had bound to the peptide (% bound) was determined by the following formula:

$$\% \text{ bound} = \frac{\text{net counts on bottom half}}{(\text{net counts on bottom half} + \text{net counts on top half})} \times 100$$

It was determined that 77% of the added $^{123}$I bound to the protein. The contents of the reaction vial were drawn into a syringe containing 1 ml isotonic saline, which was set aside for 15 minutes to be certain that oxidation of radioiodide had ceased. Into the same syringe was then drawn 0.5 cc Dowex 1×8 anion exchange resin as a 50% v/v suspension in 0.05M Tris, pH 7.4, containing 0.1M NaCl and 1 mg/ml human serum albumin. The contents of the syringe were filtered through an Acrodisc 0.2 micron luer-lock filter unit (Gelman) and the filtrate (purified radiolabeled peptide) was collected in a clean tube. The filter unit was rinsed to collect further peptide by passing a further 0.5 ml of saline through it and adding this filtrate to the purified radiolabeled peptide. Radiochemical purity of the final radiolabeled peptide solution was re-assessed by the ITLC procedure described above, and found to be 98%.

EXAMPLE 2

Preparation of $^{125}$I-bitistatin

A solution of the native bitistatins, 100 µg in 100 µl 0.05M Tris buffer pH 7.8, containing 0.1M NaCl, was placed in a clean test tube. To this solution was added 0.5 mCi $^{125}$I sodium iodide solution in a volume of 1 µl. This mixture was transferred to a microfuge tube coated on the inside walls with 100 µg Iodogen and capped with a red rubber serum stopper. The reaction was allowed to stand at room temperature for 30 minutes. Purification and assessment of final radiochemical purity were accomplished as described in Example 1 for $^{123}$I-bitistatin.

Preparation of $^{125}$I-fibrinogen control

Human fibrinogen (grade L, Kabi Diagnostika, Stockholm) was radiolabeled with $^{125}$I by the iodine monochloride technique of McFarlane, *J. Clin. Invest.* 42:346-361 (1963).

EXAMPLE 3

Preparation of $^{123}$I-Albolabrin

A solution of 25 µg albolabrin in 63 µl water was diluted by adding 65 µl 0.05M Tris buffer, pH 7.8, containing 0.1M NaCl. This solution was drawn up by syringe and added to a vial containing 12.0 mCi $^{123}$I sodium iodide solution in a volume of 39 µl. The remainder of the labeling procedure was carried out according to the procedure of Example 1. Forty-four percent of the added radioactivity was incorporated into the protein. After purification, the ITLC indicated that 87% of the activity was protein-bound.

EXAMPLE 3

Preparation of $^{123}$-Eristostatin

A solution of 50 µg eristostatin in 50 µl 0.05M Tris buffer pH 7.8, containing 0.1M NaCl, was drawn up by syringe and added to a vial containing 9.8 mCi $^{123}$I sodium iodide solution in a volume of 29 µl. The remainder of the labelling procedure was the same as in Example 1. After 30 minutes of reaction, 61.5% of the radioactivity bound to the eristostatin. Radiochemical purity of the final radiolabelled polypeptide solution assessed by ITLC was found to be 93%.

EXAMPLE 5

Clot Uptake Study in vitro

The disintegrins are incorporated into forming blood clots simultaneously as fibrin and platelets are being actively deposited in the forming clot. Disintegrins are also incorporated into existing clots in which deposition of new fibrin and platelets has ceased. Both types of clots were used in the disintegrin uptake study in vitro as follows.

Human blood was obtained from a donor (25 ml of blood anticoagulated with 5 ml of acid citrate dextrose (ACD)). The blood was transferred into 16×125 mm polystyrene tubes and centrifuged at 800 rpm in a Beckman TH-4 rotor for 15 minutes. The platelet-rich-plasma (PRP) was carefully removed with a plastic Pasteur pipet and placed in two clean polystyrene test tubes. Aliquots of PRP (200 µl each) were placed in 12×75 mm tubes. For these studies, $^{125}$I-bitistatin was diluted with isotonic saline to a concentration of 2.5 μg/ml. A concentration of bitistatin comparable to that achieved in the blood of a patient receiving a dose of 0.5 mg bitistatin was provided.

For forming clots, the following reagents were added to each aliquot of PRP, in the order listed: 10 μl of $^{125}$I bitistatin, 10 μl of 1M CaCl$_2$, and 10 μl of thrombin (100 μ/ml). The contents of each tube were observed to form a clot. The tubes containing each clot were incubated at 37° C. for 1 hour. With a wooden stick, each clot was loosened from its tube and drawn from the supernatant, pressing out excess liquid from the clot. The supernatant was saved in a tube (SUP) for scintillation counting. The clot was washed by immersion in 200 μl of 0.9% NaCl in another tube (WASH). The clot was then drained and placed in a tube (CLOT) containing 200 μl of 6M urea in 0.1M NaOH for dissolution. All three tubes (CLOT, SUP, WASH) were placed in a NaI(Tl) well counter and counted long enough so that the most radioactive tube of each set contained at least 10,000 counts.

For pre-formed clots, reagents were added to each aliquot of PRP, in the following order: 10 μl of 1M CaCl$_2$ and 10 μl of thrombin (100 μ/ml). The contents of each tube were observed to form a clot. The tubes containing each clot were incubated at 37° C. for 1 hr. With a wooden stick, each clot was loosened from its tube and drawn from the supernatant, and rinsed in 200 μl of 0.9% NaCl. Each clot was placed in a tube containing 200 μl of 0.9% NaCl to which 10 μl of $^{125}$I bitistatin has been added. The clots were incubated with the radiotracer at 37° C. for 1 hour. The clots were removed from the supernatant, washed, dissolved and counted as described for the forming clots, above. The % bound was calculated as the percent of the total activity (CLOT+SUP+WASH) which was associated with the CLOT.

The results of the study are contained in Table 1.

TABLE 1

| Type of Clot | % bound (mean + s.d.) |
|---|---|
| Forming (n = 5) | 69.1 ± 3.1 |
| Pre-formed (n = 4) | 28.4 ± 2.6 |

The results are significant since radionuclide binding above 10% to a pre-formed clot is rarely observed. The experiment demonstrated $^{125}$I-bitistatin's marked affinity for sites on the surface of the preformed clot. Radiolabelled bitistatin is capable of binding to both actively forming and pre-formed thrombi.

EXAMPLE 6

Thrombus/Embolus Uptake Study in a Dog

In this example of thrombi and emboli in a dog, the radioactivity target:background ratios were determined qualitatively by imaging and quantitatively by tissue sampling. Higher ratios are due to the increased target specificity of the radiolabel carrier. Significant measurements presented in this study are the relative ratio of counts from the target tissue (thrombus and pulmonary emboli) to background entities (muscle, vessels blood etc.). Therefore, independent target: background ratio data from the use of different isotopes in otherwise similar in vivo experiments are readily comparable. Thrombus uptake data, such as the percent injected radiolabel dose per gram of thrombus (% id/g thrombus), thrombus-to-blood (=100×% id/g thrombus ÷ %id/g blood) and thrombus-to-muscle ratios (=100×%id/g thrombus ÷ %id/g muscle) were calculated from the tissue sample count data discussed below. Significantly, there was found to be no accumulation of the radiolabelled disintegrins in the liver.

The control radiotracer, labelled fibrinogen, has been studied extensively for use as a radiolabelled compound to probe for thrombi and has previously been found to image fresh thrombi in vivo when labeled with $^{123}$I. De Nardo et al., Clin. Nucl. Med. 10, 880–883 (1985). The commercial Fibrinogen Uptake Test (FUT) for newly forming thrombi was based upon $^{125}$I-fibrinogen as the radiopharmaceutical. Fibrinogen's binding to preformed thrombi is lower than its binding to actively forming thrombi due to the decrease in availability of surface binding sites on pre-formed thrombi.

A female mongrel dog weighing 40 lbs was fasted overnight. The dog was sedated with an intramuscular injection of a mixture of ketamine hydrochloride and acepromazine maleate. General anesthesia was induced with intravenous pentobarbital (20 mg/kg). After shaving and washing the dog's skin, a 3-cm incision was made in the right groin area. Using blunt dissection, a segment of the femoral vein was located and freed from surrounding tissue for a length of 1 inch. An 18-guage angiocath was inserted into the vein, and floppy-tip guide wire was advanced through the angiocath into the vein and advanced to mid-femur (approximately 3 inches). The angiocath was replaced with a longer catheter which extended over the guidewire to mid-thigh. The guidewire was then withdrawn and an embolization coil, consisting of a stainless steel spring enmeshed with Dacron fibers and capable of expanding to a diameter of 8 mm (Cook, Bloomington, Ind.) was introduced into the catheter. The coil was advanced with the guidewire until it emerged from the distal end of the catheter, where it promptly expanded and lodged firmly in the vessel. The catheter and guide wire were withdrawn. The incision was closed with 2-0 silk. This produced a model of deep venous thrombosis.

To create a model of pulmonary embolus, an incision was made in the corresponding location on the left leg of the dog. The catheter was placed in the femoral vein as described above, except that it was advanced proximally into the inferior vena cava. A small embolization coil (3 mm expanded diameter) was released into the inferior vena cava, and embolized to the lungs. The catheter and guide wire were withdrawn. The incision was closed with 2-0 silk.

X-rays without contrast were taken of the hind leg and chest to record the positions of the coils. The dog was placed in a recovery cage with a heat lamp until it recovered from anestesia.

Twenty-four hours after placement of the coils, anesthesia was induced as before. The urinary bladder was catheterized to collect urine. A large field of view gamma camera (General Electric, Milwaukee, Wis.) was positioned over the dog for an anterior view of the chest. The camera was fitted with a low-energy all-purpose collimator and was set to acquire the 159 keV photopeak of $^{123}$I with a 20% window. A Macintosh IIx computer was interfaced to the camera using a NucLear Mac A/D board and software (Scientific Imaging, Denver, Colo.). The following radiotracers were injected into a right foreleg vein: 31 μCi of $^{125}$I-fibrinogen (358 μg), followed by a saline flush and an injection of 4.4 mCi of $^{123}$I-Bitistatin (90 μg). The $^{125}$-fibrinogen served as a control, since it has been studied previously in this dog model.

Initially, the computer was set to acquire a dynamic series of 10-sec frames for a total of 10 minutes in a 128×128 byte mode matrix. The acquisition was begun immediately before injection of the radiotracers. At hourly intervals, additional 10-sec anterior views of the chest were acquired. These static images, in addition to the dynamic series, were used to estimate the rate of blood disappearance.

Immediately after completion of the dynamic acquisition, and at approximately hourly intervals thereafter, the dog was repositioned to obtain anterior views of both hind legs. Static images were acquired in a 256×256 byte mode matrix and 500,000 counts were accumulated in each image. Additional static images of the chest were taken in the anterior, right lateral and right anterior oblique (RAO) projections for imaging of the pulmonary embolus.

At 2 hours and 45 min. post injection, deep anesthesia was induced by intravenous administration of 30 mg/kg pentobarbital. A blood sample was drawn and 0.3 cc was transferred into each of two pre-weighed tubes. The animal was euthanized with intracardiac injection of KCl saturated solution. The vein segment containing the thrombus was carefully removed and dissected to separate the thrombus, coil, Dacron fibers and vessel wall. Each of these samples was placed on tared paper and weighed (wet weight). Similar size samples of control vessel (femoral vein from the control side) and skeletal muscle (from the thigh) were also collected and weighed. The "abnormal vessel" was the sample of vein from which the thrombus was dissected. The "control vessel" was the identical control vessel from the opposite leg. The control vessel Was not injured and therefore should not have significant uptake of radiotracer. Each sample was then placed in a counting tube and counted along with a saved aliquot of the injected dose as a standard, in a well counter. After counting, samples were held for decay of $^{123}$I and recounted in a lower energy window to collect the counts from $^{125}$I.

The deep venous thrombus in the right leg was clearly visible in the image at 12 minutes post injection, and subsequent images of this thrombus continued to be focally positive as long as imaging was carried out. The pulmonary embolus was visible in images acquired at 2 hr 16 min.–2 hr 35 min. post injection. The image (FIG. 2) of both hind legs of the dog was recorded two hours after the injection of $^{123}$I-bitistatin. FIG. 1 demonstrates clear thrombus focal uptake of the radiolabelled disintegrin.

Based on analysis of the images, blood clearance of the tracer was initially very rapid, and by 1 hour post injection the circulating dose had declined to about 27% of the administered dose.

$^{123}$I-bitistatin had a higher incorporation per dose into the blood clot than did $^{125}$I fibrinogen. More than twice as much of the bitistatin dose bound to the clot than did the fibrinogen dose (Table 2).

The important characteristic of low background uptake in the injured vessel, control vessel and normal lung was also demonstrated with radiolabelled bitistatin (Table 2). Residual levels in the blood and muscle were low, resulting in high clot:blood (9.64) and clot:muscle (98.24) target:background ratios (Table 3). The percent radiolabel in the blood, based on blood specimen counting was somewhat high. The blood was not anticoagulated and may not have been a representative sample. It is probable that the amount remaining in blood is actually lower, making the thrombus:blood ratios higher. Seventeen percent of the injected dose was recovered in the cumulative urine collection during the first 2.75 hours.

TABLE 2

| Percent Injected Dose Per Gram of Tissue | | |
|---|---|---|
| Tissue Sample | I-BITIS % id/g | I-FBG % id/g |
| CLOT | 0.4309 | 0.2032 |
| P.EMBOLUS | 0.1886 | 0.2500 |
| VESSEL | 0.0424 | 0.0872 |
| CONTROL VES | 0.0176 | 0.0136 |
| BLOOD | 0.0447 | 0.0597 |
| NORM LUNG | 0.0266 | 0.0139 |
| MUSCLE | 0.0044 | 0.0029 |

TABLE 3

| Tissue to Blood and Tissue to Muscle Ratios | | | | |
|---|---|---|---|---|
| TISSUE SAMPLE | I-BITIS TISS: BLOOD | I-FBG TISS: BLOOD | I-BITIS TISS: MUSCLE | I-FBG TISS: MUSCLE |
| CLOT | 9.64 | 3.40 | 98.24 | 70.92 |
| P.EMBOLUS | 4.22 | 4.18 | 43.00 | 87.25 |
| VESSEL | 0.95 | 1.46 | 9.67 | 30.45 |
| CONTROL VES | 0.39 | 0.23 | 4.02 | 4.74 |

These data indicate several things: 1) that $^{123}$I-bitistatin is capable of binding to existing thrombi in vivo better than $^{125}$I-fibrinogen; 2) the blood disappearance rate of $^{123}$I-bitistatin is sufficiently rapid to allow imaging of thrombi in the legs and chest by 2–3 hours post injection and 3) that binding of $^{123}$I-bitistatin to non-thrombus tissues is low.

COMPARATIVE EXAMPLE 7

Comparison of Short Arg Gly Asp Containing Peptides to the Disintegrins in Dog Studies Two of the most promising radiolabelled synthetic peptides as described in Knight et al., J. Nucl. Med. 31:757 (1990) were compared to the radiolabelled disintegrins in the following study. The synthetic peptides were:

Peptide-A: (SEQ ID NO: 15)

Ala Arg Arg Ser Pro Ser Tyr Tyr Arg Gly Asp Gly Ala Gly Pro
        5                  10                 15
Tyr Tyr Ala Met Asp Tyr;
        20 which was labelled with $^{123}$I as in Example 1, and

Peptide-B: (SEQ ID NO: 16)

Ser Tyr Gly Arg Gly Asp Val Arg Gly Asp Phe Lys Cys Thr Cys
        5                  10                 15
Cys Ala;

which was labelled with $^{99m}$Tc as follows:

Tc-glucoheptonate, 70 mCi/1.3 ml, was prepared (available in kit form from Du Pont Corporation). A 0.4 ml aliquot of the solution was combined with 0.2 ml of the 100 µg peptide solution. The combined solution was incubated at 37° C. for 1 hour, resulting in over 90% of the radiolabel being incorporated into the peptide via transchelation.

The imaging ability of the small peptides was compared to that of the $^{123}$I-labelled disintegrins in the Example 6 dog model. The study protocol was the same as in Example 6, except that coils were not placed in the lungs, and the time of tissue sampling differed. The label ratios were as defined in example 6.

In Tables 4 and 5 below "FC" designates femoral clot; "PE" designates pulmonary emboli; "Time" designates the tissue sampling time after injection of radiolabelled polypeptide; "AV:CV" designates the abnormal (injured) vessel:control vessel label ratio; "T:B" designates the thrombus:blood ratio and "T:M" designates the thrombus:muscle ratio.

Experimental results are summarized in table 4 wherein all tested radiolabelled disintegrins clearly demonstrated higher binding to thrombi than did Peptide-A and Peptide-B. The highest relative amount of radiotracer injected dose bound per gram of thrombus (1.2839%) was demonstrated with the $^{123}$I-bitistatin binding to pulmonary emboli. $^{123}$I-bitistatin bound the femoral clot with 0.4309% dose per gram of target. In contrast, the short radiolabelled peptides showed 0.0090% binding at best.

TABLE 4

Percent Injected Dose Per Gram of Thrombus (% id/g)

| Polypeptide | Time (hrs) | % id/g |
| --- | --- | --- |
| $^{123}$I-bitistatin (PE) | 4 | 1.2839 |
| $^{123}$I-bitstatin (FC) | 2.75 | 0.4309 |
| $^{123}$I-eristostatin (PE) | 4 | 0.1205 |
| $^{123}$I-albolabrin (FC) | 4 | 0.0714 |
| $^{123}$I-Peptide-A (FC) | 24 | 0.0090 |
| $^{99m}$Tc-Peptide-B (FC) | 4 | 0.0084 |
| $^{99m}$Tc-Peptide-B (FC) | 4 | 0.0043 |
| $^{99m}$Tc-Peptide-B (FC) | 4 | 0.0042 |

In regard to the target:background data shown below in Table 5, thrombus:blood and thrombus:muscle label ratios should be as high as possible to enable imaging of the thrombus over the blood and muscle background. For medically acceptable imaging, a thrombus-to-blood ratio of at least 4:1 is needed in the extremities and a ratio of at least 9:1 is needed in the chest. Table 5 shows the respective disintegrin ratios which resulted from the comparative studies. The ratios corresponding to the radiolabelled disintegrins were within the medically acceptable range as opposed to those shown by Peptide-A and Peptide-B, which were not.

These signal to background ratios as shown by the labelled polypeptides of the invention in Table 5 are medically significant as thrombi-imaging radiopharmaceuticals in contrast to the same ratios regarding radiolabelled Peptide-A and Peptide-B. The highest signal to background ratios, in general, were demonstrated using $^{123}$I-bitistatin in regard to pulmonary emboli and femoral clots, respectively. The radiolabelled bitistatin ratios also demonstrated relatively low binding to the control vessels (CV). The radiolabelled disintegrins eristostatin and albolabrin also demonstrated medically significant background ratios for imaging of thrombi.

TABLE 5

(same experiments as in Table 4)
Target:Background Ratios

| Molecule | Time (hrs) | AV:CV | T:B | T:M |
| --- | --- | --- | --- | --- |
| $^{123}$I-bitistatin (PE) | 4 | 5.0 | 31.3 | 404.2 |
| $^{123}$I-bitistatin (FC) | 2.75 | 2.4 | 9.6 | 98.2 |
| $^{123}$I-eristostatin (PE) | 4 | 1.2 | 8.6 | 40.6 |
| $^{123}$I-albolabrin (FC) | 4 | 1.3 | 9.9 | 42.5 |
| $^{123}$I-Peptide-A (FC) | 24 | 0.5 | 2.0 | 5.1 |

TABLE 5-continued (same experiments as in Table 4)
Target:Background Ratios

| Molecule | Time (hrs) | AV:CV | T:B | T:M |
| --- | --- | --- | --- | --- |
| $^{99m}$Tc-Peptide-B (FC) | 4 | 1.2 | 2.0 | 6.6 |
| $^{99m}$Tc-Peptide-B (FC) | 4 | 1.5 | 2.4 | 4.6 |
| $^{99m}$Tc-Peptide-B (FC) | 4 | 1.7 | 2.3 | 8.2 |

The thrombus-to-blood ratios as demonstrated by Peptide-A and Peptide-B are insufficient for medically acceptable thrombi imaging. It is generally accepted that a thrombus-to-blood ratio of at least 4:1 is needed in the extremities and a ratio of at least 9:1 is needed in the chest, as adequately demonstrated in the study by the radiolabelled disintegrins.

Figure 2:
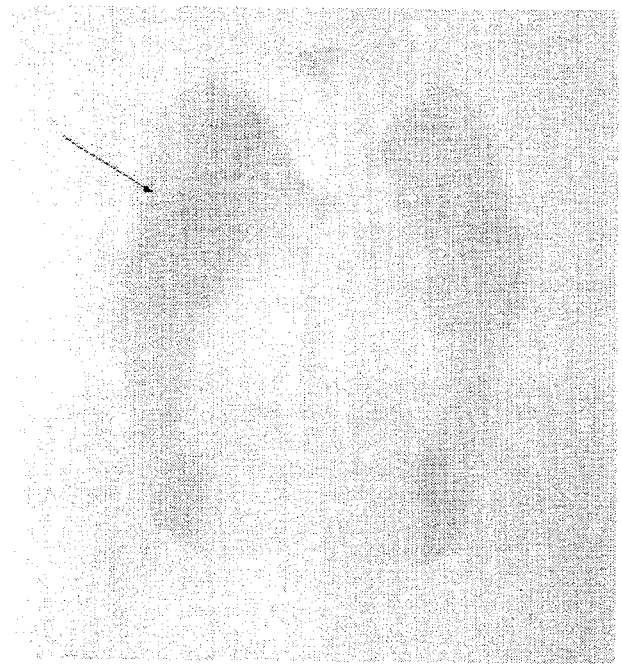
FIG. 2 is an image of both hind legs of a dog 2 hours after injection of the radiolabelled short Arg-Gly-Asp containing peptide $^{99m}$Tc-Peptide-B. There is background uptake of radiotracer in the vessels but no apparent focal uptake in the induced thrombus.

Images obtained from both Peptide-A and Peptide-B were only marginally positive in the area of the thrombus. FIG. 2 is an image of the dog's hind legs two hours post injection of $^{99m}$Tc-Peptide-B. Due to their binding to normal vascular endothelium, the short peptides showed consistent uptake in the deep veins of the normal leg. The synthetic peptide radiolabel uptake by the normal vessels is probably a consequence of the non-specificity of Peptide-A and Peptide-B. The two synthetic compounds most probably recognize sites in normal vascular endothelium.

Comparison of FIG. 1 ($^{123}$I-bitistatin, Example 6) and FIG. 2 ($^{99m}$Tc-Peptide-B) clearly demonstrates the differences in radio-imaging abilities of the radiolabelled disintegrins and the radiolabelled short peptides, respectively, in regard to deep venous thrombi.

UTILITY

The present invention includes a method for ex vivo imaging of venous thrombi, arterial thrombi, tumors and abscesses that have a thrombus component and pulmonary emboli, which comprises intravenously administering the radiolabelled polypeptides.

The detectably labelled disintegrins have unusually high affinity for activated platelets, such as those found in thrombi and emboli. They also leave the blood circulation relatively rapidly. Thus, high target-to-background ratios can be achieved shortly after injection. Very importantly, because of the rapid blood clearance and low extravascular background in the chest, pulmonary emboli are readily visible with these agents. Prior to the present invention, there has been no radiopharmaceutical available capable of reliably producing focal images of pulmonary emboli.

A significant advance is realized in nuclear medicine by the rapid and accurate diagnostic testing made possible by the present invention. The utilization of detectably labelled disintegrins in diagnostic imaging will permit physicians to expedite appropriate thrombolytic or anticoagulant therapy better tailored to specific physiological needs now discoverable due to the advantages of the radiolabelled disintegrins, the compositions for injection and the new method to image thrombi including pulmonary emboli.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

---

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 82 amino acids
( B ) TYPE: amino acid
( D ) TOPOLOGY: linear ( x i ) SEQUENCE DESCRIPTION: SEQ ID NO:1:

| Ser | Pro | Pro | Val | Cys | Gly | Asn | Glu | Leu | Glu | Glu | Gly | Glu | Glu | Cys |
|---|---|---|---|---|---|---|---|---|---|---|---|---|---|---|
|   |   |   |   | 5 |   |   |   |   | 10 |   |   |   |   | 15 |

| Asp | Cys | Gly | Ser | Pro | Ala | Asn | Cys | Gln | Asp | Arg | Cys | Cys | Asn | Ala |
|---|---|---|---|---|---|---|---|---|---|---|---|---|---|---|
|   |   |   |   | 20 |   |   |   |   | 25 |   |   |   |   | 30 |

| Ala | Thr | Cys | Lys | Leu | Thr | Pro | Gly | Ser | Gln | Cys | Asn | His | Gly | Glu |
|---|---|---|---|---|---|---|---|---|---|---|---|---|---|---|
|   |   |   |   | 35 |   |   |   |   | 40 |   |   |   |   | 45 |

| Cys | Cys | Asp | Gln | Cys | Lys | Phe | Lys | Lys | Ala | Arg | Thr | Val | Cys | Arg |
|---|---|---|---|---|---|---|---|---|---|---|---|---|---|---|
|   |   |   |   | 50 |   |   |   |   | 55 |   |   |   |   | 60 |

| Ile | Ala | Arg | Gly | Asp | Trp | Asn | Asp | Asp | Tyr | Cys | Thr | Gly | Lys | Ser |
|---|---|---|---|---|---|---|---|---|---|---|---|---|---|---|
|   |   |   |   | 65 |   |   |   |   | 70 |   |   |   |   | 75 |

| Ser | Asp | Cys | Pro | Trp | Asn | His |
|---|---|---|---|---|---|---|
|   |   |   |   | 80 |   |   |

( 2 ) INFORMATION FOR SEQ ID NO:2:

( i ) SEQUENCE CHARACTERISTICS:
( A ) LENGTH: 83 amino acids
( B ) TYPE: amino acid
( D ) TOPOLOGY: linear ( x i ) SEQUENCE DESCRIPTION: SEQ ID NO:2:

| Ser | Pro | Pro | Val | Cys | Gly | Asn | Lys | Ile | Leu | Glu | Gln | Gly | Glu | Asp |
|---|---|---|---|---|---|---|---|---|---|---|---|---|---|---|
|   |   |   |   | 5 |   |   |   |   | 10 |   |   |   |   | 15 |

| Cys | Asp | Cys | Gly | Ser | Pro | Ala | Asn | Cys | Gln | Asp | Gln | Cys | Cys | Asn |
|---|---|---|---|---|---|---|---|---|---|---|---|---|---|---|
|   |   |   |   | 20 |   |   |   |   | 25 |   |   |   |   | 30 |

| Ala | Ala | Thr | Cys | Lys | Leu | Thr | Pro | Gly | Ser | Gln | Cys | Asn | His | Gly |
|---|---|---|---|---|---|---|---|---|---|---|---|---|---|---|
|   |   |   |   | 35 |   |   |   |   | 40 |   |   |   |   | 45 |

| Glu | Cys | Cys | Asp | Gln | Cys | Lys | Phe | Lys | Lys | Ala | Arg | Thr | Val | Cys |
|---|---|---|---|---|---|---|---|---|---|---|---|---|---|---|
|   |   |   |   | 50 |   |   |   |   | 55 |   |   |   |   | 60 |

| Arg | Ile | Ala | Arg | Gly | Asp | Trp | Asn | Asp | Asp | Tyr | Cys | Thr | Gly | Lys |
|---|---|---|---|---|---|---|---|---|---|---|---|---|---|---|
|   |   |   |   | 65 |   |   |   |   | 70 |   |   |   |   | 75 |

| Ser | Ser | Asp | Cys | Pro | Trp | Asn | His |
|---|---|---|---|---|---|---|---|
|   |   |   |   | 80 |   |   |   |

( 2 ) INFORMATION FOR SEQ ID NO:3:

( i ) SEQUENCE CHARACTERISTICS:
( A ) LENGTH: 84 amino acids
( B ) TYPE: amino acid
( D ) TOPOLOGY: linear ( x i ) SEQUENCE DESCRIPTION: SEQ ID NO:3:

| Val | Ser | Pro | Pro | Val | Cys | Gly | Asn | Lys | Ile | Leu | Glu | Gln | Gly | Glu |
|---|---|---|---|---|---|---|---|---|---|---|---|---|---|---|
|   |   |   |   | 5 |   |   |   |   | 10 |   |   |   |   | 15 |

| Asp | Cys | Asp | Cys | Gly | Ser | Pro | Ala | Asn | Cys | Gln | Asp | Gln | Cys | Cys |
|---|---|---|---|---|---|---|---|---|---|---|---|---|---|---|
|   |   |   |   | 20 |   |   |   |   | 25 |   |   |   |   | 30 |

| Asn | Ala | Ala | Thr | Cys | Lys | Leu | Thr | Pro | Gly | Ser | Gln | Cys | Asn | His |

35                          40                             45
Gly Glu Cys Cys Asp Gln Cys Lys Phe Lys Lys Ala Arg Thr Val
                    50                          55                             60
Cys Arg Ile Ala Arg Gly Asp Trp Asn Asp Asp Tyr Cys Thr Gly
                    65                          70                             75
Lys Ser Ser Asp Cys Pro Trp Asn His
                    80

( 2 ) INFORMATION FOR SEQ ID NO:4:

( i ) SEQUENCE CHARACTERISTICS:
        ( A ) LENGTH: 83 amino acids
        ( B ) TYPE: amino acid
        ( D ) TOPOLOGY: linear ( x i ) SEQUENCE DESCRIPTION: SEQ ID NO:4:

Ser Pro Pro Val Cys Gly Asn Glu Ile Leu Glu Gln Gly Glu Asp
                    5                           10                             15
Cys Asp Cys Gly Ser Pro Ala Asn Cys Gln Asp Gln Cys Cys Asn
                    20                          25                             30
Ala Ala Thr Cys Lys Leu Thr Pro Gly Ser Gln Cys Asn His Gly
                    35                          40                             45
Glu Cys Cys Asp Gln Cys Lys Phe Lys Lys Ala Arg Thr Val Cys
                    50                          55                             60
Arg Ile Ala Arg Gly Asp Trp Asn Asp Asp Tyr Cys Thr Gly Lys
                    65                          70                             75
Ser Ser Asp Cys Pro Trp Asn His
                    80

( 2 ) INFORMATION FOR SEQ ID NO:5:

( i ) SEQUENCE CHARACTERISTICS:
        ( A ) LENGTH: 73 amino acids
        ( B ) TYPE: amino acid
        ( D ) TOPOLOGY: linear ( x i ) SEQUENCE DESCRIPTION: SEQ ID NO:5:

Glu Ala Gly Glu Asp Cys Asp Cys Gly Ser Pro Ala Asn Pro Cys
                    5                           10                             15
Cys Asp Ala Ala Thr Cys Lys Leu Ile Pro Gly Ala Gln Cys Gly
                    20                          25                             30
Glu Gly Leu Cys Cys Asp Gln Cys Ser Phe Ile Glu Glu Gly Thr
                    35                          40                             45
Val Cys Arg Ile Ala Arg Gly Asp Asp Leu Asp Asp Tyr Cys Asn
                    50                          55                             60
Gly Arg Asn Ser Ala Gly Cys Pro Arg Asn Pro Phe His
                    65                          70

( 2 ) INFORMATION FOR SEQ ID NO:6:

( i ) SEQUENCE CHARACTERISTICS:
        ( A ) LENGTH: 49 amino acids
        ( B ) TYPE: amino acid
        ( D ) TOPOLOGY: linear ( x i ) SEQUENCE DESCRIPTION: SEQ ID NO:6:

Glu Cys Glu Ser Gly Pro Cys Cys Arg Asn Cys Lys Phe Leu Lys
                    5                           10                             15
Glu Gly Thr Ile Cys Lys Arg Ala Arg Gly Asp Asp Met Asp Asp
                    20                          25                             30
Tyr Cys Asn Gly Lys Thr Cys Asp Cys Pro Arg Asn Pro His Lys
                    35                          40                             45

Gly Pro Ala Thr ( 2 ) INFORMATION FOR SEQ ID NO:7:

( i ) SEQUENCE CHARACTERISTICS:
       ( A ) LENGTH: 48 amino acids
       ( B ) TYPE: amino acid
       ( D ) TOPOLOGY: linear ( x i ) SEQUENCE DESCRIPTION: SEQ ID NO:7:

| Gln | Glu | Glu | Pro | Cys | Ala | Thr | Gly | Pro | Cys | Cys | Arg | Arg | Cys | Lys |
|-----|-----|-----|-----|-----|-----|-----|-----|-----|-----|-----|-----|-----|-----|-----|
|     |     |     |     | 5   |     |     |     |     | 10  |     |     |     |     | 15  |
| Phe | Lys | Arg | Ala | Gly | Lys | Val | Cys | Arg | Val | Ala | Arg | Gly | Asp | Trp |
|     |     |     |     | 20  |     |     |     |     | 25  |     |     |     |     | 30  |
| Asn | Asp | Asp | Tyr | Cys | Thr | Gly | Lys | Ser | Cys | Asp | Cys | Pro | Arg | Asn |
|     |     |     |     | 35  |     |     |     |     | 40  |     |     |     |     | 45  |
| Pro | Trp | Asn |     |     |     |     |     |     |     |     |     |     |     |     |

( 2 ) INFORMATION FOR SEQ ID NO:8:

( i ) SEQUENCE CHARACTERISTICS:
       ( A ) LENGTH: 71 amino acids
       ( B ) TYPE: amino acid
       ( D ) TOPOLOGY: linear ( x i ) SEQUENCE DESCRIPTION: SEQ ID NO:8:

| Glu | Ala | Gly | Glu | Glu | Cys | Asp | Cys | Gly | Thr | Pro | Glu | Asn | Pro | Cys |
|-----|-----|-----|-----|-----|-----|-----|-----|-----|-----|-----|-----|-----|-----|-----|
|     |     |     |     | 5   |     |     |     |     | 10  |     |     |     |     | 15  |
| Cys | Asp | Ala | Ala | Thr | Cys | Lys | Leu | Arg | Pro | Gly | Ala | Gln | Cys | Ala |
|     |     |     |     | 20  |     |     |     |     | 25  |     |     |     |     | 30  |
| Glu | Gly | Leu | Cys | Cys | Asp | Gln | Cys | Arg | Phe | Lys | Gly | Ala | Gly | Lys |
|     |     |     |     | 35  |     |     |     |     | 40  |     |     |     |     | 45  |
| Ile | Cys | Arg | Arg | Ala | Arg | Gly | Asp | Asn | Pro | Asp | Asp | Arg | Cys | Thr |
|     |     |     |     | 50  |     |     |     |     | 55  |     |     |     |     | 60  |
| Gly | Gln | Ser | Ala | Asp | Cys | Pro | Arg | Asn | Arg | Phe |     |     |     |     |
|     |     |     |     | 65  |     |     |     |     | 70  |     |     |     |     |     |

( 2 ) INFORMATION FOR SEQ ID NO:9:

( i ) SEQUENCE CHARACTERISTICS:
       ( A ) LENGTH: 62 amino acids
       ( B ) TYPE: amino acid
       ( D ) TOPOLOGY: linear ( x i ) SEQUENCE DESCRIPTION: SEQ ID NO:9:

| Val | Ala | Pro | Ala | Asn | Pro | Cys | Cys | Asp | Ala | Ala | Thr | Cys | Lys | Leu |
|-----|-----|-----|-----|-----|-----|-----|-----|-----|-----|-----|-----|-----|-----|-----|
|     |     |     |     | 5   |     |     |     |     | 10  |     |     |     |     | 15  |
| Thr | Pro | Gly | Ser | Gln | Cys | Ala | Glu | Gly | Leu | Cys | Cys | Asp | Asn | Cys |
|     |     |     |     | 20  |     |     |     |     | 25  |     |     |     |     | 30  |
| Lys | Phe | Ile | Lys | Ala | Gly | Xaa | Ile | Cys | Arg | Arg | Ala | Arg | Gly | Asp |
|     |     |     |     | 35  |     |     |     |     | 40  |     |     |     |     | 45  |
| Asn | Xaa | Xaa | Xaa | Xaa | Xaa | Xaa | Xaa | Xaa | Xaa | Xaa | Xaa | Xaa | Xaa | Xaa |
|     |     |     |     | 50  |     |     |     |     | 55  |     |     |     |     | 60  |
| Xaa | Xaa |     |     |     |     |     |     |     |     |     |     |     |     |     |

( 2 ) INFORMATION FOR SEQ ID NO:10:

( i ) SEQUENCE CHARACTERISTICS:
       ( A ) LENGTH: 71 amino acids
       ( B ) TYPE: amino acid
       ( D ) TOPOLOGY: linear ( x i ) SEQUENCE DESCRIPTION: SEQ ID NO:10:

```
Glu  Ala  Gly  Glu  Glu  Cys  Asp  Cys  Gly  Ser  Pro  Glu  Asn  Pro  Cys
                    5                        10                       15

Cys  Asp  Ala  Ala  Thr  Cys  Lys  Leu  Arg  Pro  Gly  Ala  Gln  Cys  Ala
                    20                       25                       30

Glu  Gly  Leu  Cys  Cys  Asp  Gln  Cys  Lys  Phe  Met  Lys  Glu  Gly  Thr
                    35                       40                       45

Val  Cys  Arg  Ala  Arg  Gly  Asp  Asp  Val  Asn  Asp  Tyr  Cys  Asn  Gly
                    50                       55                       60

Ile  Ser  Ala  Gly  Cys  Pro  Arg  Asn  Pro  Phe  His
                    65                       70
```

( 2 ) INFORMATION FOR SEQ ID NO:11:

( i ) SEQUENCE CHARACTERISTICS:
        ( A ) LENGTH: 68 amino acids
        ( B ) TYPE: amino acid
        ( D ) TOPOLOGY: linear ( x i ) SEQUENCE DESCRIPTION: SEQ ID NO:11:

```
Gly  Lys  Glu  Cys  Asp  Cys  Ser  Ser  Pro  Glu  Asn  Pro  Cys  Cys  Asp
                    5                        10                       15

Ala  Ala  Thr  Cys  Lys  Leu  Arg  Pro  Gly  Ala  Gln  Cys  Gly  Glu  Gly
                    20                       25                       30

Leu  Cys  Cys  Glu  Gln  Cys  Lys  Phe  Ser  Arg  Ala  Gly  Lys  Ile  Cys
                    35                       40                       45

Arg  Ile  Pro  Arg  Gly  Asp  Met  Pro  Asp  Asp  Arg  Cys  Thr  Gly  Gln
                    50                       55                       60

Ser  Ala  Asp  Cys  Pro  Arg  Tyr  His
                    65
```

( 2 ) INFORMATION FOR SEQ ID NO:12:

( i ) SEQUENCE CHARACTERISTICS:
        ( A ) LENGTH: 70 amino acids
        ( B ) TYPE: amino acid
        ( D ) TOPOLOGY: linear ( x i ) SEQUENCE DESCRIPTION: SEQ ID NO:12:

```
Gly  Glu  Glu  Cys  Asp  Cys  Gly  Ser  Pro  Glu  Asn  Pro  Cys  Cys  Asp
                    5                        10                       15

Ala  Ala  Thr  Cys  Lys  Leu  Arg  Pro  Gly  Ala  Gln  Cys  Ala  Asp  Gly
                    20                       25                       30

Leu  Cys  Cys  Asp  Gln  Cys  Arg  Phe  Lys  Lys  Lys  Arg  Thr  Ile  Cys
                    35                       40                       45

Arg  Arg  Ala  Arg  Gly  Asp  Asn  Pro  Asp  Asp  Arg  Cys  Thr  Gly  Gln
                    50                       55                       60

Ser  Ala  Asp  Cys  Pro  Arg  Asn  Gly  Leu  Tyr
                    65                       70
```

( 2 ) INFORMATION FOR SEQ ID NO:13:

( i ) SEQUENCE CHARACTERISTICS:
        ( A ) LENGTH: 70 amino acids
        ( B ) TYPE: amino acid
        ( D ) TOPOLOGY: linear ( x i ) SEQUENCE DESCRIPTION: SEQ ID NO:13:

```
Gly  Gly  Glu  Cys  Asp  Cys  Gly  Ser  Pro  Glu  Asn  Pro  Cys  Cys  Asp
                    5                        10                       15

Ala  Ala  Thr  Cys  Lys  Leu  Arg  Pro  Gly  Ala  Gln  Cys  Ala  Asp  Gly
                    20                       25                       30
```

```
Leu  Cys  Cys  Asp  Gln  Cys  Arg  Phe  Lys  Lys  Lys  Arg  Thr  Ile  Cys
               35                       40                            45

Arg  Ile  Ala  Arg  Gly  Asp  Phe  Pro  Asp  Asp  Arg  Cys  Thr  Gly  Leu
               50                       55                            60

Ser  Ala  Asp  Cys  Pro  Arg  Trp  Asn  Asp  Leu
               65                       70
```

( 2 ) INFORMATION FOR SEQ ID NO:14:

( i ) SEQUENCE CHARACTERISTICS:
        ( A ) LENGTH: 73 amino acids
        ( B ) TYPE: amino acid
        ( D ) TOPOLOGY: linear ( x i ) SEQUENCE DESCRIPTION: SEQ ID NO:14:

```
Glu  Ala  Gly  Glu  Asp  Cys  Asp  Cys  Gly  Ser  Pro  Ala  Asn  Pro  Cys
                5                       10                            15

Cys  Asp  Ala  Ala  Thr  Cys  Lys  Leu  Leu  Pro  Gly  Ala  Gln  Cys  Gly
               20                       25                            30

Glu  Gly  Leu  Cys  Cys  Asp  Gln  Cys  Ser  Phe  Met  Lys  Lys  Gly  Thr
               35                       40                            45

Ile  Cys  Arg  Arg  Ala  Arg  Gly  Asp  Asp  Leu  Asp  Asp  Tyr  Cys  Asn
               50                       55                            60

Gly  Ile  Ser  Ala  Gly  Cys  Pro  Arg  Asn  Pro  Leu  His  Ala
               65                       70
```

( 2 ) INFORMATION FOR SEQ ID NO:15:

( i ) SEQUENCE CHARACTERISTICS:
        ( A ) LENGTH: 21 amino acids
        ( B ) TYPE: amino acid
        ( D ) TOPOLOGY: linear ( x i ) SEQUENCE DESCRIPTION: SEQ ID NO:15:

```
Ala  Arg  Arg  Ser  Pro  Ser  Tyr  Tyr  Arg  Gly  Asp  Gly  Ala  Gly  Pro
                5                       10                            15

Tyr  Tyr  Ala  Met  Asp  Tyr
               20
```

( 2 ) INFORMATION FOR SEQ ID NO:16:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:16:

```
Ser  Tyr  Gly  Arg  Gly  Asp  Val  Arg  Gly  Asp  Phe  Lys  Cys  Thr  Cys
                5                       10                            15

Cys  Ala
```

We claim:

1. A method for detecting venous thrombi, arterial thrombi, pulmonary emboli, or tumors or abscesses having a thrombus component, comprising:

(a) administering to a patient at least one radiolabelled polypeptide having a native disintegrin amino acid sequence from about 40 to about 90 amino acids in length, said radiolabelled polypeptide having a thrombus-to-blood ratio of at least about 4:1 and containing the segment -Arg-Gly-Asp-, wherein the glycine residue of said segment is designated as position zero of said radiolabelled polypeptide, said radiolabelled polypeptide further comprising cysteine amino acid residues at positions $-23$, $-18$, $-17$, $-14$, $-5$, $+7$, and $+14$, relative to said glycine residue, and said radiolabelled polypeptide further comprising the following amino acid residues occurring at the following positions: Gly ($-20$), Phe ($-12$), Asp ($+4$), and Pro ($+15$); and (b) scintigraphically imaging the radiolabelled polypeptides.

2. A method according to claim 1, wherein said radiolabelled polypeptide further comprises a cysteine amino acid residue occurring at position $+12$.

3. A method according to claim 1, wherein said radiolabelled polypeptide further comprises a cysteine amino acid residue occurring at position $-31$.

4. A method according to claim 3, wherein said radiolabelled polypeptide further comprises a cysteine amino acid residue occurring at position −36.

5. A method according to claim 4, wherein said radiolabelled polypeptide further comprises a cysteine amino acid residue occurring at position −37.

6. A method according to claim 5, wherein said radiolabelled polypeptide further comprises a cysteine amino acid residue occurring at position −47.

7. A method according to claim 6, wherein said radiolabelled polypeptide further comprises a cysteine amino acid residue occurring at position −49.

8. A method according to claim 7, wherein said radiolabelled polypeptide further comprises a cysteine amino acid residue occurring at position −60.

9. A method according to claim 5, wherein said radiolabelled polypeptide further comprises a cysteine amino acid residue occurring at position −41.

10. A method according to claim 9, wherein said radiolabelled polypeptide further comprises a cysteine amino acid residue occurring at position −47.

11. A method according to claim 10, wherein said radiolabelled polypeptide further comprises a cysteine amino acid residue occurring at position −49.

12. A method according to claim 11, wherein said radiolabelled polypeptide further comprises a cysteine amino acid residue occurring at position −60.

13. A method according to claim 12, wherein the radiolabelled polypeptide has the amino acid sequence SEQ ID NO:1.

14. A method according to claim 13, wherein the radiolabelled polypeptide has the amino acid sequence SEQ ID NO:2.

15. A method according to claim 12, wherein the radiolabelled polypeptide has the amino acid sequence SEQ ID NO:3.

16. A method according to claim 12, wherein the radiolabelled polypeptide has the amino acid sequence SEQ ID NO:4.

17. A method according to claim 7, wherein the radiolabelled polypeptide has the amino acid sequence SEQ ID NO:5.

18. A method according to claim 1, wherein the radiolabelled polypeptide has the amino acid sequence SEQ ID NO:6.

19. A method according to claim 1, wherein the radiolabelled polypeptide has the amino acid sequence SEQ ID NO:7.

20. A method according to claim 7, wherein the radiolabelled polypeptide has the amino acid sequence SEQ ID NO:8.

21. A method according to claim 5, wherein the radiolabelled polypeptide has the amino acid sequence SEQ ID NO:9.

22. A method according to claim 7, wherein the radiolabelled polypeptide has the amino acid sequence SEQ ID NO:10.

23. A method according to claim 7, wherein the radiolabelled polypeptide has the amino acid sequence SEQ ID NO:11.

24. A method according to claim 7, wherein the radiolabelled polypeptide has the amino acid sequence SEQ ID NO:12.

25. A method according to claim 7, wherein the radiolabelled polypeptide has the amino acid sequence SEQ ID NO:13.

26. A method according to claim 7, wherein the radiolabelled polypeptide has the amino acid sequence SEQ ID NO:14.

27. A method according to claim 1 wherein said scintigraphically imaging comprises imaging pulmonary emboli.

* * * * *

UNITED STATES PATENT AND TRADEMARK OFFICE
CERTIFICATE OF CORRECTION

Patent No.: 5,380,646

Dated: Jan. 10, 1995

Inventor(s): Linda C. Knight *et al.*

It is certified that error appears in the above-identified patent and that said Letters Patent is hereby corrected as shown below.

Column 5, line 38, change "(III)" to -- (II) --.

Column 7, line 51, change "+15" to -- +51 --.

Column 8, line 49, change "(III)" to -- (II) --.

Column 14, line 37, change "EXAMPLE 3" to -- EXAMPLE 4 --.

Column 14, line 38, change "$^{123}$" to -- $^{123}I$ --.

Column 17, line 48, change "2)" to -- 1 --.

Column 19, line 29, change "bitstatin" to -- bitistatin --.

UNITED STATES PATENT AND TRADEMARK OFFICE
CERTIFICATE OF CORRECTION

Patent No.: 5,380,646

Dated: Jan. 10, 1995

Inventor(s): Linda C. Knight *et al.*

It is certified that error appears in the above-identified patent and that said Letters Patent is hereby corrected as shown below.

Please amend the sequence listings as follows:

Delete SEQ ID NO:1 and insert therefor:

-- (2) INFORMATION FOR SEQ ID NO:1:

(i) SEQUENCE CHARACTERISTICS:
        (A) LENGTH: 83 amino acids
        (B) TYPE: amino acid
        (C) STRANDEDNESS:
        (D) TOPOLOGY: linear (ii) MOLECULE TYPE: other nucleic acid (xi) SEQUENCE DESCRIPTION: SEQ ID NO:1:

```
Ser Pro Pro Val Cys Gly Asn Glu Leu Leu Glu Glu Gly Glu Glu Cys
 1               5                  10                      15

Asp Cys Gly Ser Pro Ala Asn Cys Gln Asp Arg Cys Cys Asn Ala Ala
             20                  25                  30

Thr Cys Lys Leu Thr Pro Gly Ser Gln Cys Asn His Gly Glu Cys Cys
         35                  40                  45

Asp Gln Cys Lys Phe Lys Lys Ala Arg Thr Val Cys Arg Ile Ala Arg
     50                  55                  60

Gly Asp Trp Asn Asp Asp Tyr Cys Thr Gly Lys Ser Ser Asp Cys Pro
 65                  70                  75                  80

Trp Asn His --
```

UNITED STATES PATENT AND TRADEMARK OFFICE
CERTIFICATE OF CORRECTION

Patent No.: 5,380,646

Dated: Jan. 10, 1995

Inventor(s): Linda C. Knight *et al.*

It is certified that error appears in the above-identified patent and that said Letters Patent is hereby corrected as shown below.

Delete SEQ ID NO:2 and insert therefor:

```
-- (2) INFORMATION FOR SEQ ID NO:2:

(i) SEQUENCE CHARACTERISTICS:
        (A) LENGTH: 83 amino acids
        (B) TYPE: amino acid
        (C) STRANDEDNESS:
        (D) TOPOLOGY: linear (ii) MOLECULE TYPE: other nucleic acid (xi) SEQUENCE DESCRIPTION: SEQ ID NO:2:

Ser Pro Pro Val Cys Gly Asn Lys Ile Leu Glu Gln Gly Glu Asp Cys
    1               5                   10                  15

Asp Cys Gly Ser Pro Ala Asn Cys Gln Asp Arg Cys Cys Asn Ala Ala
                    20                  25                  30

Thr Cys Lys Leu Thr Pro Gly Ser Gln Cys Asn His Gly Glu Cys Cys
            35                  40                  45

Asp Gln Cys Lys Phe Lys Lys Ala Arg Thr Val Cys Arg Ile Ala Arg
        50                  55                  60

Gly Asp Trp Asn Asp Asp Tyr Cys Thr Gly Lys Ser Ser Asp Cys Pro
    65                  70                  75                  80

Trp Asn His --
```

UNITED STATES PATENT AND TRADEMARK OFFICE
CERTIFICATE OF CORRECTION

Patent No.: 5,380,646

Dated: Jan. 10, 1995

Inventor(s): Linda C. Knight *et al.*

It is certified that error appears in the above-identified patent and that said Letters Patent is hereby corrected as shown below.

Delete SEQ ID NO:5 and insert therefor:

-- (2) INFORMATION FOR SEQ ID NO:5:

(i) SEQUENCE CHARACTERISTICS:
        (A) LENGTH: 72 amino acids
        (B) TYPE: amino acid
        (C) STRANDEDNESS:
        (D) TOPOLOGY: linear (ii) MOLECULE TYPE: other nucleic acid (xi) SEQUENCE DESCRIPTION: SEQ ID NO:5:

```
Glu Ala Gly Glu Asp Cys Asp Cys Gly Ser Pro Ala Asn Pro Cys Cys
1               5                   10                  15

Asp Ala Ala Thr Cys Lys Leu Ile Pro Gly Ala Gln Cys Gly Glu Gly
                20                  25                  30

Leu Cys Cys Asp Gln Cys Ser Phe Ile Glu Glu Gly Thr Val Cys Arg
        35                  40                  45

Ile Ala Arg Gly Asp Asp Leu Asp Asp Tyr Cys Asn Gly Arg Ser Ala
        50                  55                  60

Gly Cys Pro Arg Asn Pro Phe His
65                  70                  --
```

UNITED STATES PATENT AND TRADEMARK OFFICE
CERTIFICATE OF CORRECTION

Patent No.: 5,380,646

Page 5 of 6

Dated: Jan. 10, 1995

Inventor(s): Linda C. Knight *et al.*

It is certified that error appears in the above-identified patent and that said Letters Patent is hereby corrected as shown below.

Delete SEQ ID NO:12 and insert therefor:

```
-- (2) INFORMATION FOR SEQ ID NO:12:

(i) SEQUENCE CHARACTERISTICS:
        (A) LENGTH: 72 amino acids
        (B) TYPE: amino acid
        (C) STRANDEDNESS:
        (D) TOPOLOGY: linear (ii) MOLECULE TYPE: other nucleic acid (xi) SEQUENCE DESCRIPTION: SEQ ID NO:12:

Glu Ala Gly Glu Glu Cys Asp Cys Gly Ser Pro Glu Asn Pro Cys Cys
   1               5                   10                  15

Asp Ala Ala Thr Cys Lys Leu Arg Pro Gly Ala Gln Cys Ala Asp Gly
                   20                  25                  30

Leu Cys Cys Asp Gln Cys Arg Phe Lys Lys Lys Arg Thr Ile Cys Arg
               35                  40                  45

Arg Ala Arg Gly Asp Asn Pro Asp Asp Arg Cys Thr Gly Gln Ser Ala
           50                  55                  60

Asp Cys Pro Arg Asn Gly Leu Ser                                --
   65                  70
```

UNITED STATES PATENT AND TRADEMARK OFFICE
CERTIFICATE OF CORRECTION

Patent No.: 5,380,646

Dated: Jan. 10, 1995

Inventor(s): Linda C. Knight *et al.*

It is certified that error appears in the above-identified patent and that said Letters Patent is hereby corrected as shown below.

Claim 14, line 32, change "13" to -- 12 --.

Signed and Sealed this

Twenty-second Day of December, 1998

*Attest:*

BRUCE LEHMAN

*Attesting Officer*  Commissioner of Patents and Trademarks